(12) United States Patent
Jeanne-Rose et al.

(10) Patent No.: US 6,737,047 B2
(45) Date of Patent: May 18, 2004

(54) USE OF AN ORGANOMETALLIC COMPOUND TO PROTECT AND/OR STRENGTHEN A KERATIN MATERIAL, AND TREATMENT PROCESS

(75) Inventors: Valérie Jeanne-Rose, Paris (FR); Francis Xavier Quinn, Paris (FR)

(73) Assignee: L'Oreal S.A., Paris (FR)

( * ) Notice: Subject to any disclaimer, the term of this patent is extended or adjusted under 35 U.S.C. 154(b) by 20 days.

(21) Appl. No.: 09/902,660

(22) Filed: Jul. 12, 2001

(65) Prior Publication Data

US 2003/0012756 A9 Jan. 16, 2003

(30) Foreign Application Priority Data

Jul. 13, 2000 (FR) .............................. 00 09224

(51) Int. Cl.$^7$ ................................. A61K 7/04
(52) U.S. Cl. ................. 424/61; 424/47; 424/70.2; 424/70.1; 424/70.7; 514/937; 514/938; 514/944

(58) Field of Search ................ 424/61, 47, 70.1, 424/70.7, 70.12, 70.2; 514/937, 938, 944

(56) References Cited

FOREIGN PATENT DOCUMENTS

EP 0159628 * 10/1985

OTHER PUBLICATIONS

WO 98/44906, Abstract (Oct. 15, 1998).
WO 00/53153 Abstract (Sep. 14, 2000).

* cited by examiner

*Primary Examiner*—Jyothsna Venkat
(74) *Attorney, Agent, or Firm*—Finnegan, Henderson, Farabow, Garrett & Dunner, L.L.P.

(57) ABSTRACT

The use of a composition comprising at least one organometallic compound which may be obtained by partial or total hydrolysis, and partial or total condensation, of at least one metallic precursor, to at least one of protect and strengthen a keratin material.

21 Claims, No Drawings

USE OF AN ORGANOMETALLIC COMPOUND TO PROTECT AND/OR STRENGTHEN A KERATIN MATERIAL, AND TREATMENT PROCESS

The present invention relates to the use of materials obtained, for example, by hydrolysis and condensation of metal alkoxides, for the cosmetic treatment of a keratin material, such as the nails.

It is well known that the nails often have structural and consistency defects, which may have a variety of causes, in particular associated with the individual's internal functioning, living conditions, eating habits, age and states of fatigue and overwork. These defects may also appear due to the effect of eroding actions, for example, following prolonged or repeated exposure to detergents, solvents, chemical products and in particular household chemical products, hot or cold, humid or dry atmospheres, or exposure to UV radiation. These structural and consistency defects have the effect of making the surface of the nails unattractive, which may be a source of inconvenience and of great displeasure.

Various types of compositions essentially based on the use of either agents for crosslinking proteins intended to strengthen the keratin network, such as, for example, formaldehyde, or of agents with an essentially nutrient function such as, for example, cystine, cholesterol, S-carboxymethylcysteine or collagen extracts, have already been proposed for the purpose of strengthening the nails. However, using such crosslinking agents or such agents with a nutrient function may not give good results and, what is more, may have certain drawbacks. For example, formaldehyde-based products may cause certain allergic reactions. It has also been proposed to use colloidal silicic acid as an agent for reinforcing keratin material, for example, the nails, but also the hair and the eyelashes. These compositions improve the quality of the nails, that is to say they make them less fragile, less brittle or less soft. However, most of the existing compositions may need to be applied several times before an effect may be observed. In addition, depending on the nature of the reinforcing agent used, it may be necessary to avoid contact with water, since the effect may not withstand prolonged soaking of the nails. This may be due to the fact that the reinforcing agents according to the prior art act only at the surface of the keratin materials.

There is still thus a need to have available a cosmetic composition which, by simple application to a keratin material such as the nails, eyelashes, eyebrows, body hairs or head hair, makes it possible to accomplish at least one of the following: improve the quality of these materials very quickly, protect the materials, strengthen the materials, rapidly and durably improve the rigidity of the materials, and rapidly and durably improve the cohesion of the materials.

In accordance with the invention, one aim of the present invention is to propose such a composition, which makes it possible to accomplish at least one of the following: improve the quality of a keratin material very quickly, protect the material, strengthen the material, rapidly and durably improve the rigidity of the material, and rapidly and durably improve the cohesion of the material.

One subject of the present invention is thus the use of a composition comprising at least one organometallic compound to at least one of protect and strengthen a keratin material. The at least one organometallic compound may, for example, be obtained by at least one of partial and total hydrolysis, and partial and total condensation, of at least one metallic precursor chosen from those described below.

Another subject of the invention is a process for treating a keratin material, such as to protect and/or strengthen the keratin material, which comprises applying to the keratin material a composition comprising at least one organometallic compound. The at least one organometallic compound may, for example, be obtained by at least one of partial and total hydrolysis, and partial and total condensation, of at least one metallic precursor as defined below.

When a composition according to the invention is applied to the nails, it may make it possible to reduce the brittleness of the nails, especially of weakened nails, for example, of striated, cracked, soft or supple nails and/or nails which have a tendency to split.

At least one additional object and advantage of the invention will be set forth in part in the description which follows, and in part will be obvious from the description, or may be learned by practice of the invention.

It is to be understood that both the foregoing general description and the following detailed description are exemplary and explanatory only and are not restrictive of the invention, as claimed.

It has been found that the application to the surface of the nail of at least one embodiment of the composition of the invention increases at least one of the rigidity and cohesion of the nail, and may do so from the first application; moreover, this effect may persist over time and may be water-remanent. In at least one embodiment, the use of a composition produce harder and stronger, and thus less brittle nails. This strengthening of nail keratin also gives nails which no longer split and/or crack.

When a composition according to the invention is intended to be applied to the hair, it may allow the hair, such as soft hair, to be rigidified and thus for the styling of this hair to be improved.

The use of at least one embodiment of the invention thus finds an application for treating fragile, brittle or soft nails, but also for normal nails, or for the eyelashes, the eyebrows and the hair.

Without being bound by the present explanation, it is thought that, in at least one embodiment of the invention, this is due to the formation, within the keratin material, of a three-dimensional network generated by the organometallic compound, which is reflected by an increase in the material's hardness or rigidity.

Moreover, in certain embodiments of the invention, a composition according to the present invention may give the keratin material at least one other property, such as an optical effect, a surface effect, for example, a surface smoothness or a change in the wettability of the surface.

A composition which is used in the context of the present invention thus comprises, for example, in a cosmetically acceptable medium, at least one organometallic compound which may, for example, be obtained by at least one of partial and total hydrolysis and partial and total condensation of at least one metallic precursor chosen from:

(1) at least one metal alkoxide chosen from formulae (Ia), (Ib), (Ic), and (Id):

$$M\text{—}(OR_1)_n \quad\quad (Ia)$$

$$R\text{—}M\text{—}(OR_1)_{n-1} \quad\quad (Ib)$$

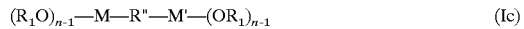
$$(R_1O)_{n-1}\text{—}M\text{—}R''\text{—}M'\text{—}(OR_1)_{n-1} \quad\quad (Ic)$$

$$RR'\text{—}M'(OR_1)_{n-2} \quad\quad (Id)$$

in which:

M and M', which may be identical or different, denote a metal atom chosen from the transition metals of groups Ib to VIIb* of the Periodic Table, group VIII* of the Periodic Table, the lanthanide group of the Periodic Table, aluminum, silicon, boron, tin, magnesium, alkali metals and alkaline-earth metals;

n denotes the valency of the metal;

$R_1$, which may be identical or different, is chosen from linear and branched, saturated and unsaturated hydrocarbon-based radicals containing 1 to 30 carbon atoms, for example, such as from 1 to 6 carbon atoms, optionally interrupted by and/or substituted with 1–20 hetero atoms chosen from O, N, S and P;

R and R', which may be identical or different, are chosen from hydrogen and linear, branched, and cyclic, saturated and unsaturated, $C_{1-30}$ hydrocarbon-based radicals, such as $C_{2-20}$ hydrocarbon-based radicals, optionally substituted and/or interrupted with 1–20 hetero atoms chosen from O, N, S and P; and/or optionally substituted with a group chosen from the list below; or R and/or R', which may be identical or different, are chosen from and/or substituted by cosmetically active groups as defined below;

R" is chosen from —O—, —NR²—, —S— and linear, cyclic and branched, saturated and unsaturated, $C_{1-C30}$ divalent hydrocarbon-based radicals, such as $C_{2-C20}$ hydrocarbon-based radicals, optionally substituted with a group chosen from the list below; and/or optionally interrupted and/or substituted with 1–20 hetero atoms chosen from O, N, P and/or S, also being chosen from and/or substituted by cosmetically active groups as defined below, wherein $R^2$ is chosen from hydrogen, linear, cyclic and branched, saturated and unsaturated $C_{1-30}$ hydrocarbon-based radicals, such as $C_{2-20}$ hydrocarbon-based radicals;

(2) the at least one complex chosen from at least one of the formulae (IIa), (IIb), (IIc) and (IId) below:

(IIa)

(IIb)

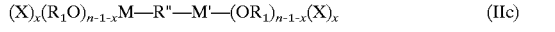(IIc)

(IId)

in which:

M, M', n, R, R', R" and $R_1$ have the same meaning as above;

X, which may be identical or different, is chosen from a ligand comprising an atom chosen from nitrogen, phosphorus, sulphur and oxygen, said ligand optionally bearing a cosmetically active group as defined below;

x is the number of atoms which may link to the central metal atom;

(3) at least one metal halide chosen from formulae (IIIa), (IIIb), (IIIc) and (IIId) below:

(IIIa)

(IIIb)

(IIIc)

(IIId)

in which:

M, M', n, R, R' and R" have the same meaning as above;

Z, which may be identical or different, is chosen from a halogen atom such as chlorine, iodine, bromine or fluorine; and (4) at least one complex chosen from formulae (IVa), (IVb), (IVc) and (IVd) below:

(IVa)

(IVb)

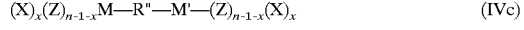(IVc)

(IVd)

in which:

M, M', n, R, R', R", X, x and Z have the same meaning as above.

According to the present invention, the term "ligand" means a group comprising at least one atom which can link to the central metal atom.

Among the substituents which may be borne by R, R' and/or R", mention may be made of halogen atoms (chlorine, bromine, iodine and/or fluorine) and the following groups: —NR₂, —CO—NR₂, —SR, —R—S—R, —CO₂R, —COR, —OH, —N=C=O, —NR—CO—NR₂, —N⁺R₃, —S⁺=C (NR₂)₂; sulphonate (—SO₃R);

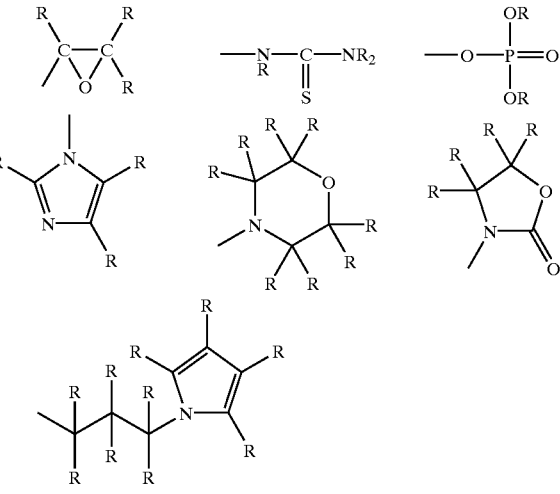

in which the various radicals R, which may be identical or different, are chosen from hydrogen and linear, branched and cyclic, saturated and unsaturated, $C_{1-30}$ hydrocarbon-based radicals, such as $C_{2-20}$ hydrocarbon-based radicals.

Among the cosmetically active groups which may be represented and/or borne by R, R', and R" and borne by X, mention may be made of a colorant group; a photochromic group; a group for screening out UV-A and/or UV-B radiation; a group for promoting adhesion to keratin materials, such as an amide, urethane, urea, hydroxyl, carboxyl, amino acid or polypeptide group; a group which facilitates make-up removal; a bacterial or bacteriostatic group; a chelating group, for example, one which can complex multivalent cations; a hydroxy acid; a group for preventing hair loss; an antioxidant group; a free-radical-scavenging group; and a vitamin-bearing group.

For example, the at least one metallic precursor may be chosen from at least one compound chosen from formulae (Ia), (Ib), (Ic), (Id) and (IIa), and, as a further example, from formulae (Ia), (Ib) and (IIa).

The metal atom M, for example, may be chosen from titanium, zirconium, aluminium, iron, tin and silicon and as a further example, from titanium and silicon.

For example, $R_1$ may be chosen from linear and branched, saturated hydrocarbon-based radicals containing 1 to 30 carbon atoms, such as, in a further example, from 1 to 6 carbon atoms. As even a further example, $R_1$ may be chosen from methyl, ethyl, propyl, n-butyl, isobutyl and t-butyl radicals.

For example, R and R', which may be identical or different, may be chosen from linear or branched, saturated $C_{1-20}$ hydrocarbon-based radicals, such as $C_{1-6}$ hydrocarbon-based radicals; or, as a further example, from linear or branched, saturated $C_{1-20}$ hydrocarbon-based radicals, such as $C_{1-6}$ hydrocarbon-based radicals, substituted with at least one substituent chosen from a halogen atom (such as perfluorinated), —$NH_2$, —CO—$NH_2$, —SH, —$CO_2H$, —COR, —OH, —N=C=O, —NH—CO—$NH_2$, —$N^+R_3$, such as, —$N^+Bu_3$, —*=C$(NH_2)_2$; benzenesulphonate;

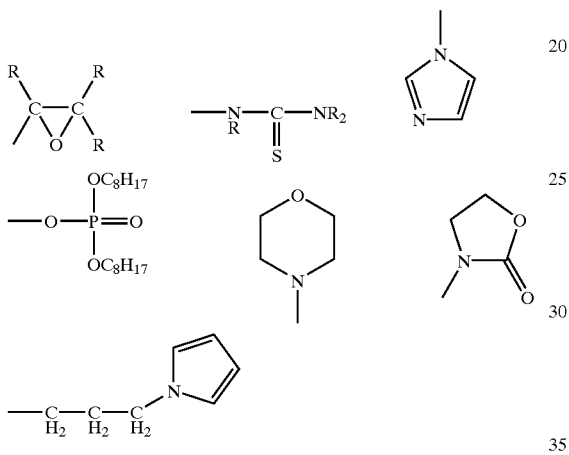

in which the various radicals R, which may be identical or different, are chosen from hydrogen and linear, branched and cyclic, saturated or unsaturated, $C_{1-30}$ hydrocarbon-based radicals, such as $C_{2-20}$ hydrocarbon-based radicals.

For example, R" may be chosen from —O—, —NH— and linear and branched, saturated $C_{1-30}$ divalent hydrocarbon-based radicals, such as $C_{2-20}$ divalent hydrocarbon-based radicals, optionally interrupted with at least one hetero atom chosen from O, N, P and S.

For example, X may be chosen from carboxylic acids, sulphonic acids, phosphonic acids, phosphoric acids, sulphuric acids, ketones, β-diketones, esters, β-keto esters, amines, β-keto amines, amino acids, such as α- and β-hydroxylated amino acids and derivatives thereof, α- and β-hydroxylated acids, ethers and polyethers, imines, amides, said amides being optionally hydroxylated, azo compounds, thiols, ureidos, thioether sulphoxides, thioether sulphones, optionally cyclic thioethers, di (thioethers), monoalcohols and polyols, dextrin and its derivatives, thiazolidines; hydrocarbon-based polymers optionally comprising hetero atoms chosen from N, O, S and P, said polymers, being obtained, for example, by free-radical polymerization, by condensation or by controlled "living" polymerization, and said polymers having a (weight-average) molecular weight ranging from 90 to 10 000, such as, for example, from 100 to 1 000, and as a further example from 150 to 500; and derivatives thereof.

Mention may be made, for example, of:
salicylic acid and its derivatives such as 4-(meth)-acrylaminosalicylic acid and 5-(meth) acrylamidosalicylic acid;

lactic acid; succinic acid; acetic acid; citric acid;

acrylic acid esters or methacrylic acid esters, such as acetoxyethyl (meth) acrylate; methyl α-hydroxy (meth) acrylate;

ethyl acetoacetate of formula $CH_3$—CO—$CH_2$—COOCH$_2$CH$_3$, methyl acetoacetate of formula $CH_3$—CO—$CH_2$—COOCH$_3$ and acetylacetone of formula $CH_3$—CO—$CH_2$—CO—$CH_3$;

EDTA;

low molecular weight polyethers (n ranging from 1 to 12) such as poly (ethylene glycols) and poly (propylene glycols);

lysine and its derivatives, such as ε—N-(meth) acryloyl-L-lysine;

cysteine and its derivatives, such as N-acetylcysteine, N-acetylcysteine disulphides and carboxymethylcysteine;

cystine; methionine;

lactic acid esters or acetic acid esters triethanolamine;

cysteine and its derivatives;

lipoic acids;

dextrin and cyclodextrin;

polymers of polyethylene glycol, polypropylene glycol or polyethyleneimine type; and diketones such as 2,4-pentanedione, 2,4-hexafluoropentanedione or 2,2,6,6-tetramethyl-3,5-heptanedione.

For example, the at least one metallic precursor, according to the invention, is chosen from:

tetramethoxysilane, silicon, titanium or tin tetraethoxide; titanium, silicon or tin tetraisopropoxide; tin, titanium or silicon tetrabutoxide;

methyltriethoxysilane, methyltrimethoxysilane, mercaptopropyltriethoxysilane, 3-aminopropyl-triethoxysilane; allyltriethoxysilane;

N-triethoxysilylpropyl-N,N,N-tri-n-butylammonium chloride of formula $(C_4H_9)_3N^+CH_2CH_2CH_2Si(OC_2H_5)_3$, Cl$^-$ N-triethoxysilylpropyl-N,N,N-tri-n-butylammonium bromide of formula $(C_4H_9)_3N^+CH_2CH_2CH_2Si(OC_2H_5)_3$, Br$^-$ N-(trimethoxysilylpropyl) isothiouronium chloride of formula $(NH_2)_2C=S^+CH_2CH_2CH_2Si(OCH_3)_3$, Cl$^-$ (3-glycidyloxypropyl) trimethoxysilane;

(3-(2-aminoethylamino) propyl) trimethoxysilane;

(3-(2-(2-aminoethylamino) ethylamino) propyl) trimethoxysilane;

(4-aminobutyl) triethoxysilane;

(N-(6-aminohexyl) aminopropyl) trimethoxysilane;

(N-methylaminopropyl) trimethoxysilane;

acetoxymethyltriethoxysilane;

3-triethoxysilylpropylurea;

triethoxysilane (3-aminopropyl) methyldiethoxysilane;

(mercaptomethyl) methyldiethoxysilane;

(3-mercaptopropyl) methyldimethoxysilane;

titanium diisopropoxide bis (triethanolamine) of formula $[(HOCH_2CH_2)_2NCH_2CH_2O]_2Ti(OC_3H_7)_2$ methyldiethoxysilane, methyldimethoxysilane, allyldimethoxysilane;

titanium diisopropoxide bis (2,4-pentanedionate) of formula:

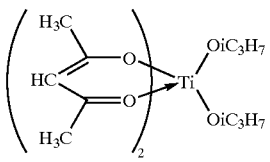

zirconium diisopropoxide bis (2,2,6,6-tetramethyl-3,5-heptanedionate); and bis (2,4-pentanedionato) titanium-O, O'-bis(oxyethyl) aminopropyltriethoxysilane.

The at least one organometallic compound used in the context of the present invention may be obtained, for example, by partial or total hydrolysis, and partial or total condensation, of at least one metallic precursor as defined above, according to a well-known sol-gel process.

In general, but in a non-limiting manner, the at least one metallic precursor may initially be dissolved or dispersed in a co-solvent such as an oil of plant, mineral, organic or synthetic origin, such as those described below, and/or an alcohol, monoalcohol or polyol, for example, ethanol, such as those described below.

A hydrolysis reaction can then be carried out either by adding water or by means of the residual water, or by adding water "generators" (in which case the water will be generated in situ). A chelating compound may also optionally be introduced.

A sol of the desired at least one organometallic compound can thus be obtained, which may be in the form of colloidal particles suspended in the co-solvent, or in the form of a compound dissolved in the co-solvent. The colloidal particles are generally nanometer-sized, such as from about 0.2 to 100 nanometers, for example, from 0.5–50 nm and from 1–10 nm.

In the rest of the present description, the expression "organometallic compound sol" will mean the mixture of the organometallic compound and of its co-solvent.

For example, the organometallic compound sol has a solids content of 1–95% by weight, for example, 3–90% by weight and 4–60% by weight. The solids content is measured after heating the sol at 100° C. for 1 hour at ambient pressure (1 atm).

The co-solvent which may be used may be chosen from alcoholic solvents, such as $C_{1-10}$ alcohols, such as methanol, ethanol, isopropanol, n-propanol, n-butanol, isobutanol, t-butanol, n-pentanol and hexanol; polyols such as propylene glycol, ethylene glycol, pentylene glycol, glycerol and sorbitol; and Miglyol®.

It is also possible to add 0–99.9% by weight water to the alcoholic solvent in order to obtain an aqueous-alcoholic mixture.

Co-solvents which may also be used include, for example:
ketones such as acetone, methyl ethyl ketone, methyl isobutyl ketone, diisobutyl ketone, isophorone and cyclohexanone;
glycol ethers, such as propylene glycol monomethyl ether, propylene glycol monomethyl ether acetate and dipropylene glycol aminobutyl ether;
aldehydes;
esters, such as acetates, for example butyl, propyl, ethyl, isopropyl, isopentyl and 2methoxyethyl acetates, purcellin oil, and isopropyl myristate;
esters of mineral acid and of alcohol;
linear and branched, optionally aromatic, hydrocarbons, such as hexane, octane, hexadecane, heptanes, dedicate, cyclohexanone, liquid paraffin, xylene and toluene, polydecenes, and hydrogenerated polyisobutene such as parleam; and
ethers and polyethers.

It is also possible to use polar or apolar, volatile and/or non-volatile cosmetically acceptable oils, for example of plant, mineral, animal and/or synthetic origin, among which mention may be made, alone or as a mixture, of:
hydrocarbon-based oils of animal origin, such as perhydrosqualene;
hydrocarbon-based plant oils, such as liquid fatty acid triglycerides, for example sunflower oil, corn oil, soybean oil, marrow oil, grapeseed oil, jojoba oil sesame oil, hazelnut oil, apricot oil, macadamia oil, castor oil, avocado oil, olive oil, wheat germ oil, sweet almond oil, beauty-leaf oil or palm oil, caprylic/capric acid triglycerides such as those sold by the company Stearineries Dubois or those sold under the names Miglyol 810, 812 and 818 by the company Dynamit Nobel;
fatty alcohols containing from 10 to 32 carbon atoms, for example octyldodecanol, 2-butyloctanol, 2-hexyldecanol, 2-undecylpentadecanol or oleyl alcohol;
partially hydrocarbon-based and/or silicone-based fluoro oils;
silicone-based oils, for example poly($C_1$-$C_{20}$) alkylsiloxanes, such as polyalkylmethylsiloxanes and further such as volatile and non-volatile, linear and cyclic polydimethylsiloxanes (PDMSs), such as cyclotetradimethylsiloxane, cyclopentadimethylsiloxane and cyclohexadimethylsiloxane; silicones modified with aliphatic and/or aromatic groups, which may be fluorinated, or with functional groups such as hydroxyl, thiol and/or amine groups; phenylsilicone oils such as polyphenylmethylsiloxanes or phenyltrimethicones; and
volatile hydrocarbon-based oils, such as isoparaffins, for example, isododecane and isohexadecane.

The organometallic compound sol may be used without further modification as a cosmetic composition.

It is also possible to add to a composition of the present invention comprising the organometallic compound sol the constituents usually used in the intended field of application.

For example, a composition of the present invention may comprise at least one film-forming material which may be chosen, for example, from alkyd, acrylic and/or vinyl resins, polyurethanes, polyester-polyurethanes, polyether-polyurethanes, free-radical polymers such as acrylic, styrene-acrylic and/or vinyl polymers, polyesters, celluloses and cellulose derivatives such as nitrocellulose, and resins resulting from the condensation of formaldehyde with an arylsulphonamide.

The at least one said film-forming material may be in solution or in a dispersion in water and/or in an organic solvent such as toluene, xylene, ethyl acetate and/or butyl acetate, ketones, glycol ethers, esters and alcohols such as ethanol, isopropanol or butanol, and mixtures thereof.

A composition of the present invention may also comprise at least one plasticizer and optionally at least one rheological agent. Among the plasticizers which may be mentioned are citrates, phthalates, esters and/or camphor. Among the rheological agents which may be mentioned are organophilic bentonites, cellulose derivatives, crosslinked polyacrylic acid derivatives, guar gums, carob gums and xanthan gums.

When a composition of the present invention is in the form of an emulsion, it may comprise at least one conventional emulsifier chosen from amphoteric, anionic, cationic and nonionic emulsifiers.

A composition of the present invention may also comprise a particulate phase, which may comprise organic or mineral pigments, and/or nacres and/or fillers usually used in cosmetic compositions. Mention may be made, for example, of titanium dioxide, zirconium dioxide, cerium dioxide, zinc oxide, iron oxide, chromium oxide and ferric blue; carbon black and barium, strontium, calcium or aluminium lacks; mica coated with titanium oxide, with iron oxide, with natural pigment or with bismth oxychloride; colored titanium mica and natural mother-of-pearl, talc, mica, silica, kaolin, Nylon powder, polyethylene powder, Teflon, starch, boron nitride, microspheres such as Expancel (Nobel Industrie), Polytrap (Dow Corning) and silicone resin microbeads (for example Tospearls from Toshiba).

A composition according to the invention may also comprise any additive known to those skilled in the art as being able to be incorporated in such a composition, such as spreading agents, thickeners, wetting agents, dispersants, antifoams, preserving agents, surfactants, UV screening agents, colorants, cosmetic active agents, vitamins and derivatives thereof, ceramides, trace elements, moisturizers such as glycerol, waxes, gums, essential oils, DNA and fragrances. Needless to say, a person skilled in the art will take care to select this or these optional additional compound(s), and/or the amount thereof, such that at least one of the advantageous properties provided by the invention are not, or are not substantially, adversely affected by the addition envisaged.

For example, a composition which may be used in the context of the present invention comprises 1% to 100% by weight of organometallic compound sol, such as 1.5% to 95% by weight. In embodiments of the present invention, a composition comprises 10–90% by weight of organometallic compound sol and may comprise 12–50% by weight of organometallic compound sol.

A composition according to the invention may be prepared by a person skilled in the art on the basis of his general knowledge and according to applicable techniques from the prior art.

A composition of the invention may be, for example, in the form of an aqueous, organic or aqueous-alcoholic solution or suspension; an oil-in-water, water-in-oil or multiple emulsion, such as a cream or a milk, an aqueous or oily gel; a dispersion, a composition to be sprayed; a patch.

The keratin material which may be treated according to the invention may be chosen, for example, from the toenails, the fingernails, the eyelashes, the eyebrows, body hairs and head hair.

A composition according to the invention may thus be in the form of a make-up composition, such as a mascara or a treating mascara; a nail varnish, a varnish base or a nailcare product; a haircare composition, such as a styling lacquer, lotion or mousse, a styling spray or a styling stick.

EXAMPLE 1

Ethanol and water at pH 1 were introduced into a reactor equipped with a magnetic bar, a condenser and a dropping funnel. The mixture was placed under magnetic stirring for 15 minutes at 30° C. 10.4 g (0.05 mol) of tetraethoxysilane were added dropwise thereto with continued stirring for 48 hours. The reaction mixture was finally poured into a flask and placed at 30° C. The composition (or sol) thus obtained may be stored without further modification, so as to incorporate it subsequently into a cosmetic composition.

EXAMPLE 2

Ethanol and water at pH 1 were introduced into a reactor equipped with a magnetic bar, a condenser and a dropping funnel. The mixture was placed under magnetic stirring for 15 minutes at 30° C. 11 g (0.05 mol) of aminopropyltriethoxysilane were added dropwise thereto and vigorous stirring was maintained for 48 hours. The reaction mixture was finally poured into a flask and placed at 30° C. The composition thus obtained was stored without further modification, so as to incorporate it subsequently into a cosmetic composition.

EXAMPLE 3

Ethanol and water at pH 1 were introduced into a reactor equipped with a magnetic bar, a condenser and a dropping funnel. The mixture was placed under magnetic stirring for 15 minutes at 30° C. 8.9 g (0.05 mol) of methyltriethoxysilane were added dropwise thereto and vigorous stirring was maintained for 48 hours. The reaction mixture was finally poured into a flask and placed at 30° C. The composition thus obtained was stored without further modification, so as to incorporate it subsequently into a cosmetic composition.

EXAMPLE 4

A dynamic flexural characterization was carried out on nails treated with the compositions of Examples 2 and 3 and with a comparative commercial hardening composition "Durcilong" from Gemey.

The dynamic flexural characterization made it possible to determine the viscoelastic properties of a material in terms of elasticity and viscosity.

It consists in imposing a repeated sinusoidal stress (displacement) of small amplitude $\Delta l$ on a sample. The sample reacted to the stress by opposing a sinusoidal force of amplitude $\Delta F$, which was phase-shifted relative to the stress by an angle $\delta$.

The viscoelastic nature of the material may be characterized by the modulus of stiffness K (N/m) which corresponds to the overall rigidity of the sample, as may be determined by pulling or crushing the sample; and by the loss of angle $\delta$ (in degrees) which characterizes the intrinsic viscosity. The greater the loss angle, the greater the viscosity of the material and the more delayed the material's response of the material and the more delayed the material's response to the stress.

$$K(N/m) = \frac{\Delta F}{\Delta l}$$

Samples of natural human nails were cut with scissors into the shape of a 4 mm×5 mm rectangle.

Before any measurement, they were left for 48 hours in a glove box at a temperature of 25° C. and under a relative humidity of 45%.

3 drops of the compositions prepared in Example 2 and 3 were applied to the samples using a micropipette.

The treated samples were then left for 24 hours in a glove box at a temperature of 25° C. and under relative humidity of 45%, in order for the solvent to evaporate completely.

For each of the samples, the value of the modulus of stiffness K and the loss angle $\delta$ was determined before and after treatment.

A Metravib VA 2000 viscoelasticimeter was used, which allows measurements to be taken directly in the glove box (T=25° C.; R.H.=45%).

The sample was gripped in fixing jaws via the "root side" of the end of the nail. The dynamic measuring head of the viscoelasticimeter repeatedly stresses the free end (opposite edge) of the nail by means of a knife. A constant (flexural) deformation, on which was superimposed a sinusoidal stress—the wave flexure—was applied to the nail. The nail remained overall always flexed in the same direction.

The conditions were as follows:
  static displacement: $d_{stat}=-300\ \mu m$ approximately, which corresponds to a static force F of 0.6 N
  amplitude of the dynamic displacements: $d_{dyn}=\pm 30\ \mu m$ approximately
  sinusoidal stress frequency: f=10 Hz The value of ΔF, and thus of K, and of δ, were determined before treatment, after 1 day and after 7 days of treatment. The values of ΔK and of Δδ were deduced therefrom, after 1 and 7 days.

$$\Delta K(\%) = \frac{K_{after} - K_{before}}{K_{before}} \times 100$$

$$\Delta \delta(\%) = \frac{\delta_{after} - \delta_{before}}{\delta_{before}} \times 100$$

The following result were obtained:

| | K before treatment (N/m) | K after 1 day (N/M) | K After 7 days (N/m) | ΔK (1 day) | ΔK (7 days) |
|---|---|---|---|---|---|
| Example 2 (solids content 10.2%) | 6830 | 7770 | 8090 | 13.76 | 18.45 |
| Example 3 (solids content 5.9) | 6930 | 7490 | 7770 | 8.08 | 12.12 |
| Durcilong (solids content 13%) | 8770 | 9910 | 10300 | 13.00 | 17.44 |

| | δ before treatment | δ after 1 day | δ After 7 days | Δδ (1 day) | Δδ (7 days) |
|---|---|---|---|---|---|
| Example 2 (solids content 10.2%) | 2.9 | 4.2 | 4.0 | 44.83 | 37.93 |
| Example 3 (solids content 5.9) | 2.8 | 3.2 | 3.4 | 14.29 | 21.43 |
| Durcilong (solids content 13%) | 3.3 | 6.5 | 6.1 | 96.97 | 84.85 |

It was thus found that the compounds of Examples 2 and 3 gave results that were comparable, in terms of rigidification, with those obtained with a commercial nail-strengthening product, for lower solids contents.

EXAMPLE 5

Vickers hardness measurements were carried out on nails treated with the composition Example 2 above.

The measurement was carried out in the following way:

Nails samples were collected from several donors. They were cut into small rectangles 2 to 3 mm wide in the median longitudinal part and 3 to 4 mm long approximately.

Three fragments were bonded to a rectangular stainless steel support using an adhesive of "cyanolite" type. 3 plots were prepared per product, i.e. 9 fragments. The samples were then conditioned at a relative humidity of 75% and at a temperature of 30° C., for 48 hours.

A first measurement was carried out on the untreated samples.

Next, 0.5 μl per $mm^2$ of the test composition was applied to each nail fragment. The fragments were then conditioned at a relative humidity of 75% and at a temperature of 30° C. for 48 hours.

The Vickers hardness coefficient (VH) was determined using an M 400 G2 Leco® microdurometer, with the following conditions:
  application load: 50 gf
  application time: 15 sec
  application speed: 60 μm/sec The following results were obtained:

| | Vickers hardness (VH) |
|---|---|
| Untreated Nails | 16 |
| Nails treated with the composition of Example 2 | 18 |

An increased of about 12.5% in the hardness of the nails treated with the composition according to the invention was thus observed.

EXAMPLE 6

A composition was prepared comprising, on a weight basis:

| | |
|---|---|
| thickener | 2% |
| colorant | 0.2% |
| preserving agent, fragrance | Qs |
| composition of Example 1 | qs 100% |

A composition which may be applied to the nails was obtained.

What is claimed is:

1. A method of protecting and/or strengthening a keratin material comprising applying to said keratin material a composition comprising at least one organometallic compound obtained from at least one metal alkoxide

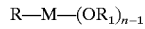   R—M—(OR$_1$)$_{n-1}$   (Ib)

wherein:
  M denotes a metal atom chosen from the transition metals of groups Ib to VIIb of the Periodic Table, group VIII of the Periodic Table, the lanthanide group of the Periodic Table, aluminum, silicon, boron, tin, magnesium, alkali metals and alkaline-earth metals;
  n denotes the valency of the metal;
  $R_1$, which may be identical or different, is chosen from linear and branched, saturated and unsaturated hydrocarbon-based radicals containing 1 to 30 carbon atoms,
  R is chosen from hydrogen, and linear, branched and cyclic, saturated and unsaturated $C_{1-30}$ hydrocarbon-based radicals; and
  wherein said composition is applied to said keratin material in an amount effective to obtain at least one of harder nails, stronger nails, less brittle nails, nails which no longer split, and nails which no longer crack.

2. A method according to claim 1, wherein said at least one organometallic compound is obtained by at least one of partial and total hydrolysis of said at least one metallic precursor and partial and total condensation of said at least one metallic precursor.

3. A method according to claim 1, wherein $R_1$ is chosen from linear and branched, saturated and unsaturated hydrocarbon-based radicals containing 1 to 6 carbon atoms, optionally interrupted by and/or substituted with 1–20 hetero atoms chosen from O, N, S and P.

4. A method according to claim 1, wherein R and R', which may be identical or different, are chosen from hydrogen, and linear, branched and cyclic, saturated and unsaturated $C_{2-20}$ hydrocarbon-based radicals, optionally substituted and/or interrupted with 1–20 hetero atoms chosen from O, N, S and P.

5. A method according to claim 1, wherein of R is substituted with at least one substituent chosen from a halogen atom, $-NR_2$, $-CO-NR_2$, $-SR$, $-R-S-R$, $-CO_2R$, $-COR$, $-OH$, $-N=C=O$, $-NR-CO-NR_2$, $-NR_3$, $-S^+=C\ (NR_2)_2$; sulphonate ($-SO_3R$);

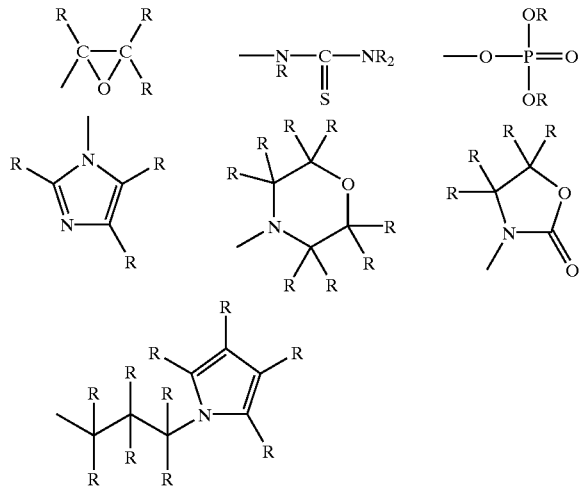

wherein R, which may be identical or different, are chosen from hydrogen and linear, branched and cyclic, saturated and unsaturated, $C_{1-30}$ hydrogen-based ridicals.

6. A method according to claim 1, wherein said amount is effective to at least one of quickly and durably improved the rigidity of said keratin material and quickly and durably improve cohesion of said keratin material.

7. A method according to claim 6, wherein said amount is effective to quickly and durably improve the cohesion of said keratin material.

8. a method according to claim 6, wherein said amount is effective to quickly and durably improve the cohesion of said keratin material.

9. A method according to claim 6, wherein said amount is effective to quickly and durably improve the rigidity and the cohesion of said keratin material.

10. A method according to claim 1, wherein said keratin material is chosen from the toenails and the fingernails.

11. A method according to claim 1, wherein said amount is effective to reduce the brittleness of weakened nails.

12. A method according to claim 11, wherein said amount is effective to reduce the brittleness of weakened nails chosen from striated nails, cracked nails, soft nails, supple nails, and nails which have a tendency to split.

13. A method according to claim 1, wherein said metal atom M is chosen from titanium, zirconium, aluminum, iron, tin, and silicon.

14. A method according to claim 13, wherein said metal atom M is chosen from titanium and silicon.

15. A method according to claim 1, wherein said at least one metallic precursor is chosen from:

methyltriethoxysilane, methltrimethoxysilane, mercaptorpropylyiethoxysilane, 3-aminopropyl-triethoxysilane; and allyltriethoxyysilane.

16. A method according to claim 1, wherein said composition comprises a sol of said at least one organometallic compound.

17. A method according to claim 16, wherein said composition comprises 1% to 100% by weight of said organometallic compound sol.

18. A method according to claim 16, wherein said composition comprises 1.5% to 95% by weight of said organometallic compound sol.

19. A method according to claim 16, wherein said composition comprises 10% to 90% by weight of said organometallic compound sol.

20. A method according to claim 16, wherein said composition comprises 12% to 50% by weight of said organometallic compound sol.

21. A process for treating a keratin material which comprises applying to said keratin material a composition comprising at least one organometallic compound obtained from:

at least one metal alkoxide below:

$$R-M-(QR_1)_{n-1} \quad (Ib)$$

wherein:

M denotes a metal atom chosen from the transition metals of groups Ib to VIIb of the Periodic Table, group VIII of the Periodic Table, the lanthanide group of the Periodic Table, aluminum, silicon, boron, tin, magnesium, alkali metals and alkaline-earth metals;

n denotes the valency of the metal;

$R_1$, which may be identical or different, is chosen from linear and branched, saturated and unsaturated hydrocarbon-based radicals containing 1 to 30 carbon atoms, R is chosen from hydrogen, linear, branched and cyclic, saturated and unsaturated, and $C_{1-30}$ hydrocarbon-based radicals; and wherein said composition is applied to said keratin material in an amount effective to reduce the brittleness of human nails.

* * * * *

UNITED STATES PATENT AND TRADEMARK OFFICE
CERTIFICATE OF CORRECTION

PATENT NO. : 6,737,047 B2
DATED : May 18, 2004
INVENTOR(S) : Valérie Jeanne-Rose et al.

It is certified that error appears in the above-identified patent and that said Letters Patent is hereby corrected as shown below:

Column 12,
Line 47, "from at least one metal alkoxide" should read -- from:
at least one metal alkoxide chosen from formula (Ib) below: --.

Column 13,
Line 22, "-NR$_3$," should read -- -N$^+$R$_3$, --.
Line 46, "hydrogen-based ridicals." should read -- hydrocarbon-based radicals. --.
Line 48, "improved" should read -- improve --.
Line 51, "cohesion" should read -- rigidity --.
Line 53, "a method" should read -- A method --.

Column 14,
Line 15, "methltrimethoxysilane," should read -- methyltrimethoxysilane, --.
Line 16, "mercaptorpropylyiethoxysilane," should read
-- mercaptopropyltriethoxysilane, --.
Line 17, "allyltriethoxyysilane." should read -- allyltriethoxysilane. --.
Line 37, "alkoxide below:" should read -- alkoxide chosen from formula (Ib) below: --.
Line 39, "R-M-(QR$_1$)$_{n-1}$" should read -- R-M-(OR$_1$)$_{n-1}$ --.

Signed and Sealed this

Twenty-second Day of March, 2005

JON W. DUDAS
*Director of the United States Patent and Trademark Office*